(12) United States Patent
Cho et al.

(10) Patent No.: US 8,029,801 B2
(45) Date of Patent: Oct. 4, 2011

(54) HN EPITOPE RECOGNIZED BY AVIAN IMMUNE SYSTEM AND ANTIGENIC VARIANT NEWCASTLE DISEASE VIRUSES CARRYING CHANGES IN THE EPITOPE

(75) Inventors: Sun-Hee Cho, Seongnam-si (KR);
Hyuk-Joon Kwon, Seoul (KR);
Young-Jin Ahn, Gwangmyeong-si (KR);
Sun-Joong Kim, Gwacheon-si (KR);
Young-Ho Park, Yesan-gun (KR);
Chae-Hyun Kim, Yesan-gun (KR);
Tae-Hwan Kim, Yesan-gun (KR);
Tae-Eun Kim, Seoul (KR)

(73) Assignees: KBNP, Inc., Dugok-Ri, Sinam-Myeon, Chungcheongnam-Do Yesan-Gun (KR);
Biopoa, Inc., Suwonsi (KR)

( * ) Notice: Subject to any disclaimer, the term of this patent is extended or adjusted under 35 U.S.C. 154(b) by 294 days.

(21) Appl. No.: 11/995,278

(22) PCT Filed: Mar. 23, 2006

(86) PCT No.: PCT/KR2006/001068
§ 371 (c)(1),
(2), (4) Date: Jan. 10, 2008

(87) PCT Pub. No.: WO2007/108568
PCT Pub. Date: Sep. 27, 2007

(65) Prior Publication Data
US 2009/0155310 A1 Jun. 18, 2009

(51) Int. Cl.
*A61K 39/17* (2006.01)
*C07K 7/06* (2006.01)
*C12N 7/00* (2006.01)

(52) U.S. Cl. .................. 424/214.1; 424/186.1; 530/327; 435/235.1

(58) Field of Classification Search .......................... None
See application file for complete search history.

(56) References Cited

OTHER PUBLICATIONS

Gotoh et al (Virology 163:174-182, 1988).*
Sakaguchi et al (Virology 169:260-272, 1989).*
Nishikawa, K. et al. "Monoclonal antibodies as functional probes of the HN glycoprotein of Newcastle disease virus. Biological characterization and use for strain comparisons" Virology, Oct. 30, 1983, vol. 130, No. 2, pp. 318-330.
Cormam, J.J., et al. "Characterization of the sites of proteolytic activation of Newcastle disease virus membrane glycoprotein precursors" L Biol Chem., Sep. 5, 1988, vol. 263, No. 25, pp. 12522-12531.
NCBI Accession No. AAY56377 and AAY56378 (Jan. 1, 2005).
Cho, Sun-Hee et al., "Characterization of New Castle Virus type VII having HN antigenic variant of linear epitope", The 49th annual Meeting of the Korean Society of Veterinary Science, Korean Socienty of Verterinary Science Coperation, Sep. 23, 2005.

* cited by examiner

*Primary Examiner* — Mary E Mosher
(74) *Attorney, Agent, or Firm* — Lexyoume IP Group, PLLC

(57) ABSTRACT

The present invention relates to an epitope of HN protein in Newcastle disease virus which can be recognized by an avian immune system and an antibody against the epitope, a method for detecting a Newcastle disease virus by using the antibody, and an antigenic variant of Newcastle disease virus carrying changes in the epitope. The epitope of HN protein and the antigenic variant of Newcastle disease virus can be used for developing efficient vaccines, and further, in diagnosing the Newcastle disease virus rapidly and exactly.

4 Claims, 11 Drawing Sheets

FIG. 5A

Newcastle disease virus SNU0202 Hemagglutinin-Neuraminidase
(SEQ ID NO: 2)

```
gcttcggaca tctgcaacag ggagggtatt cttttctact ctgcgctcca tcaatttaga      60
tgacacccaa aatcggaagt cctgcagtgt gagtgcaacc cctttaggtt gtgatatgct     120
gtgctctaag gtcacaggga ctgaagagga ggattacaag tcagttgccc ccacatcaat     180
ggtgcacgga aggctagggt ttgacggtca ataccatgaa aaggacttag acaccacggt     240
cttatttaag gattgggtgg caaattaccc aggagcggga ggagggtctt ttattgacga     300
ccgtgtatgg ttcccagttt acggagggct caaacccaat tcacccagtg acactgcaca     360
agaagggaaa tacgtaatat acaagcgcca taacaacaca tgccccgatg aacaagatta     420
ccaaattcgg atggctaagt cttcatataa acccgggcga tttggtggaa agcgcgtaca     480
gcaagccatc ttatccatca aagtgtcaac atccttgggt aaggacccgg tgctga        536
```

FIG. 5B

Newcastle disease virus SNU5005 Hemagglutinin-Neuraminidase (SEQ ID NO: 6)

```
gcttcggaca tctgcaacag ggagggtatt cttttctact ctgcgctcca tcaatttaga      60
tgacacccaa aatcggaagt cctgcagtgt gagtgcaacc cctttaggtt gtgatatgct     120
gtgctccaag gtcacaggga ctgaagagga ggattacaag tcagttgccc ccacatcaat     180
ggtgcacgga aggctagggt ttgacggtca ataccatgaa aaggacttag acaccacggt     240
cttatttaag gattgggtgg caaattaccc aggagcggga ggagggtctt ttattgacga     300
ccgtgtatgg ttcccagttt acggagggct caaacccgat tcacccagtg acactgcaca     360
agaagggaaa tacgtaatat acaagcgcca taacaacaca tgccccgata aacaagatta     420
ccaaattcgg aaggctaagt cttcatataa acccggcga tttggtggga agcgcataca     480
gcaagccatc ttatccatca aagtgtcaac atccttgggt aaggacccgg tgctga         536
```

FIG.5C

Newcastle disease virus SNU5009 Hemagglutinin-Neuraminidase (SEQ ID NO: 6)

```
gcttcggaca tctgcaacag ggagggtatt cttttctact ctgcgctcca tcaatttaga      60
tgacacccaa aatcggaagt cctgcagtgt gagtgcaacc cctttaggtt gtgatatgct     120
gtgctccaag gtcacaggga ctgaagagga ggattacaag tcagttgccc ccacatcaat     180
ggtgcacgga aggctagggt ttgacggtca ataccatgaa aaggacttag acaccacggt     240
cttatttaag gattgggtgg caaattaccc aggagcggga ggagggtctt ttattgacga     300
ccgtgtatgg ttcccagttt acggagggct caaacccgat tcacccagtg acactgcaca     360
agaagggaaa tacgtaatat acaagcgcca taacaacaca tgccccgata acaagatta     420 ccaaattcgg aaggctaagt cttcatataa acccggcga tttggtggga agcgcataca    480
gcaagccatc ttatccatca aagtgtcaac atccttgggt aaggacccgg tgctga        536
```

FIG. 5D

Newcastle disease virus SNU5070 Hemagglutinin-Neuraminidase (SEQ ID NO: 4)

```
gcttcggaca tctgcaacag ggagggtatt cttttctact ctgcgctcca tcaatttaga      60
tgacacccaa aatcggaagt cctgcagtgt gagtgcaacc cctttaggtt gtgatatgct     120
gtgctctaag gtcacaggga ctgaagagga ggattacaag tcagttgccc ccacatcaat     180
ggtgcgcgga aggctagggt ttgacggtca ataccatgaa aaggacttag acaccacggt     240
cttatttaag gattgggtgg caaattaccc aggagcggga ggagggtctt ttattgacga     300
ccgtgtatgg ttcccagttt acggagggct caaacccaat tcacccagtg acaccacaca     360
agaagggaaa tacgtaatat acaagcgcca taacaacaca tgccccgata aacaagatta     420
ccaaattcgg atggctaagt cttcatataa acccaggcga tttggtggaa agcgcgtaca     480
gcaagccatc ttatccatca aagtgtcaac atccttgggt aaggacccgg tgctga        536
```

FIG. 5E

Newcastle disease virus SNU5074 Hemagglutinin-Neuraminidase (SEQ ID NO: 6)

```
gcttcggaca tctgcaacag ggagggtatt cttttctact ctgcgctcca tcaatttaga      60
tgacacccaa aatcggaagt cctgcagtgt gagtgcaacc cctttaggtt gtgatatgct     120
gtgttccaag gtcacaggga ctgaagagga ggattacaag tcagttgccc ccacatcaat     180
ggtgcacgga aggctagggt ttgacggtca ataccatgaa aaggacttag acaccacggt     240
cttatttaag gattgggtgg caaattaccc aggagcggga ggagggtctt ttattgacga     300
ccgtgtatgg ttcccagttt acggagggct caaacccgat tcacccagtg acactgcaca     360
agaagggaaa tacgtaatat acaagcgcca taacaacaca tgtcccgata aacaagatta     420
ccaaattcgg aaggctaagt cttcatataa acccgggcga tttggtggga agcgcgtaca     480
gcaagccatc ttatccatca aagtgtcaac atccttaggt aaggacccgg tgctga         536
```

FIG.5F

Newcastle disease virus KBNP-4152 Hemagglutinin-Neuraminidase (SEQ ID NO: 6)

```
gcttcggaca tctgcaacag ggagggtatt cttttctact ctgcgctcta tcaatttaga      60
tgacacccaa aatcggaagt cctgcagtgt gagtgcaacc cctttaggtt gtgatatgct     120
gtgctccaag gtcacaggga ctgaagagga ggattacaag tcagttgccc ccacatcaat     180
ggtgcacgga aggctaggt ttgacggtca ataccatgaa aaggacttag acaccacggt      240
cttatttaag gattgggtgg caaattaccc aggagcggga ggagggtctt ttattgacga     300
ccgtgtatgg ttcccagttt acggagggct caaacccgat tcacccagtg acactgcaca     360
agaagggaaa tacgtaatat acaagcgcca taacaacaca tgccccgata aacaagatta     420
ccaaattcgg aaggctaagt cttcatataa acccgggcga tttggtggga agcgcgtaca     480
gcaagccatc ttatccatca aagtgtcaac atctttgggt aaggacccgg tgctga         536
```

HN EPITOPE RECOGNIZED BY AVIAN IMMUNE SYSTEM AND ANTIGENIC VARIANT NEWCASTLE DISEASE VIRUSES CARRYING CHANGES IN THE EPITOPE

BACKGROUND OF THE INVENTION (a) Field of the Invention

The present invention relates to an epitope of HN protein in Newcastle disease virus which can be recognized by an avian immune system and an antibody against the epitope, a method for detecting a Newcastle disease virus by using the antibody, an antigenic variant of Newcastle disease virus carrying changes in the epitope, and a vaccine prepared by using the antigenic variant.

(b) Description of the Related Art

Newcastle disease is very infectious and lethal in fowls and thus is designated as the first communicable disease by law in Korea. If an unimmunized chicken is infected, the mortality is 100%. An infection to Egg-laying hen which is not properly immunized shows a respiratory or a digestive disorder, and reduction of laying eggs, thereby doing economic damage on poultry man. Although the occurrence of Newcastle disease is notified annually, it increases continuously and is spread all over the nation. In addition, the chicken which has a low titer of antibody in spite of immunization shows nervous system disorder such as torticolis.

Newcastle disease virus is a single stranded RNA virus belonging to genus *Avulavirus*. The envelope of Newcastle disease virus includes Haemagglutinin-Neuraminidase (HN) protein which makes the virus bind to a host, and Fusion (F) protein which makes the envelope fuse with the host cell. F and HN proteins are glycoprotein and distributed on the surface of viral envelope.

Depending on the phylogenetic analysis of the F protein in Newcastle disease virus, the Newcastle disease virus can be classified into genotype I to genotype VIII. Genotypes VI and VII are reported in Asia including Indonesia, China, Taiwan, and Japan. The genotype VII virus is classified into sub-genotypes VIIa and VIIb which were reported in Asia and Africa, respectively (Herczeg et al., 1999). In Korea, genotype VIIa virus was reported, and linear epitopes of the HN proteins have the same amino acid sequence as those of vaccine virus (Kwon et al., 2003; Lee et al., 2004). A part of Chinese genotype VII viruses cannot be prevented by conventional vaccine completely, but the reason was not reported (Yu et al., 2001).

F protein belongs to type I membrane glycoprotein and includes trimeric structure (Gorman et al., 1988; Russell et al., 1994; Reitter et al., 1995). HN protein belongs to type II membrane glycoprotein and includes tetramer on the surface of virus envelope, so as to invade into the cell membrane (Gorman et al., 1988; Ng et al., 1989). F protein has thirteen (13) cysteine residues and five (5) glycosylation sites, and HN protein has fourteen (14) cysteine residues and four (4) glycosylation sites.

Cysteine residue in protein plays an important role in protein conformation and its oligomerization. In addition, the cysteine residue has an influence on epitope formation and the glycosylation site of a peptide. Mutation on cysteine residue, C123 of HN protein does not form the disulfide bond between molecules, and covalent dimer. In addition, the mutation on cysteine residue affects a structure of antigen (McGinnes and Morrison, 1994, 1997). All Newcastle disease viruses have well-conserved cysteine residues, and it means a strict interaction between the structure and function. Biological function of each cysteine residue in F protein have not been revealed. Only C199 and C76 form a disulfide bond which maintains the linkage between F1 and F2 polypeptides after cleavage of F protein (Wang et al., 1992).

F and HN proteins are important protective antigens, and their epitopes were determined by using mouse monoclonal antibody. Until now, three conformational epitopes in F protein and two conformational epitopes in HN protein, and a linear epitope were reported (Nishikawa et al., 1983, 1986; Sakaguchi et al., 1989). Eight amino acids constituting a linear epitope of HN protein are $_{346}$Aspartic acid-Glutamic acid-Glutamine-Aspartic acid-Tyrosine-Glutamine-Isoleucine-Arginine$_{353}$.

Because F and HN proteins are important protective antigens of Newcastle disease virus, an infection and death caused by Newcastle disease virus can be prevented by immunizing fowls with F and HN proteins as antigens. In addition, the avian serum test can be carried out by using the antibodies against F and HN proteins. Particularly, the antibody against HN protein is used all over the world in hemagglutination-inhibition test. The hemagglutination-inhibition test is preferred because of high relationship between titer of antibody and disease protection, but has a disadvantage in variation of antibody titer, and difficult automation compared to the ELISA test. ELISA is advantageous in automation and measuring the reaction result as a numerical value. However, because ELISA uses all virus antigens, more antibodies to abundant nucleocapsid protein lowers the correlation with antibody titer obtained by the hemagglutination method.

SUMMARY OF THE INVENTION

The present inventors found epitope of HN protein which can be recognized by avian immune system and which may be useful for developing vaccine, and a Newcastle disease virus including mutated linear epitope, in order to prevent damage of antigenic variant Newcastle disease virus which is not completely protected by conventional vaccines.

An object of the present invention is to provide HN protein epitope of Newcastle disease virus, an antibody and its fragment against the HN protein epitope, and a detection method or a detection kit of Newcastle disease virus by using the antibody and its fragment. Another object of the present invention is to provide a new Newcastle disease virus including the mutated epitope of HN protein, a vaccine against the virus, feed stuff or feed stuff additive comprising the virus.

To achieve the objects, the present invention provides a polypeptide which is an epitope of Newcastle disease virus HN protein and comprises an amino acid sequence selected from the group consisting of an amino acid sequence having SEQ ID NO: 2, an amino acid sequence having SEQ ID NO: 4, and an amino acid sequence having SEQ ID NO: 6. The polypeptide is an amino acid sequence consisting of 345th amino acid to 358th amino acid of Newcastle disease virus HN protein.

In another embodiment, the present invention provides a Newcastle disease virus having an accession number KCTC 10919BP comprising an epitope of HN protein having an amino acid sequence as shown in SEQ ID NO: 6.

In still another embodiment of the invention, the present invention provides a vaccine for Newcastle disease comprising a Newcastle disease virus deposited as an accession number KCTC 10919BP comprising an epitope of HN protein having an amino acid sequence as shown in SEQ ID NO: 6. The vaccine is a live vaccine, an attenuated vaccine, or a killed vaccine. The vaccine can be used as a feed stuff or an additive of feed stuff.

In yet another embodiment of the invention, the present invention provides an antibody or its fragment which specifically recognizes an epitope of HN protein in Newcastle disease virus and comprises an amino acid sequence selected from the group consisting of an amino acid sequence having SEQ ID NO: 2, an amino acid sequence having SEQ ID NO: 4, and an amino acid sequence having SEQ ID NO: 6. The antibody is monoclonal or polyclonal.

In further embodiment, the present inventions provides a method of diagnosing Newcastle disease comprising the steps of reacting the antibody or its fragment with a sample, detecting a positive reaction against the antibody and determining the sample showing the positive reaction as Newcastle disease.

In still another embodiment, the present invention provides a method of diagnosing Newcastle disease or detecting Newcastle disease virus comprising the steps of reacting with the antibody or its fragment with a sample, performing haemagglutination inhibition test with the addition of chicken erythrocyte, and determining the sample showing haemagglutination inhibition as Newcastle disease virus.

In further embodiment, the present invention provides a polypeptide kit of diagnosing Newcastle disease comprising the antibody or its fragment.

In further embodiment, the present invention provides a polynucleotide kit of diagnosing Newcastle disease or detecting Newcastle disease virus comprising a polynucleotide of SEQ ID NO: 1, a polynucleotide of SEQ ID NO: 3, and a polynucleotide of SEQ ID NO: 5.

DETAILED DESCRIPTION OF THE PREFERRED EMBODIMENTS

Hereinafter, the present invention will be described in more detail.

14 amino acids including $345^{th}$ amino acid to $358^{th}$ amino acid of the HN protein constitutes a polypeptide which is a linear epitope of HN protein in Newcastle disease virus. The HN protein epitope of the present invention has a superior antigenic properties to the conventional 8 amino acid peptide of $_{346}$Aspartic acid-Glutamic acid—Glutamine-Aspartic acid-Tyrosine-Glutamine-Isoleucine-Arginine$_{353}$. The epitope activity of conventional eight amino acid peptide has been investigated by using mouse monoclonal antibody. However, the mouse immune system is totally different from that of fowls, and thus the investigated epitope cannot be necessarily an epitope recognized by avian. The HN protein epitope including 14 amino acids according to the present invention is recognized by avian immune system and has excellent immunogenicity.

The present inventors isolated RNA from highly-pathogenic Newcastle disease virus which was screened in Korea, performed RT-PCR and nucleotide sequence analysis, and deduced from the nucleotide sequence to amino acid sequence. As a result, the amino acid sequences of HN protein linear epitope are an amino acid sequence having SEQ ID NO: 2, an amino acid sequence having SEQ ID NO: 4, and an amino acid sequence having SEQ ID NO: 6. The nucleotide sequences encoding the amino acid sequences are shown in SEQ ID NO: 1, SEQ ID NO: 3, and SEQ ID NO: 5. In addition, the linear epitopes including an amino acid sequence having SEQ ID NO: 2, SEQ ID NO: 4 or SEQ ID NO: 6 were compared with those of vaccine strain, domestic and foreign Newcastle disease virus.

Consequently, HN linear epitope of SNU0202 has an amino acid sequence of SEQ ID NO: 2 which is the same as that of vaccine strain. SNU5070 has HN linear epitope of SEQ ID NO: 4. KBNP-4152, SNU5005, SNU5009, and SNU5074 have a novel amino acid sequence of SEQ ID NO: 6 (see FIG. 1). The HN linear epitope of SEQ ID NO: 6 has not been found in type VII foreign strains.

In an embodiment, the peptides of SEQ ID NO: 2 and SEQ ID NO: 6 are synthesized with Fmoc-chemistry, coated on 96-well plate, immunized with anti-La Sota strain serum which is obtained by immunizing La Sota vaccine strain including SEQ ID NO: 1, and anti-KBNP-4152 antiserum which is obtained by immunizing KBNP-4152 strain including SEQ ID NO: 3, and then performed with ELISA.

Figure 2A:
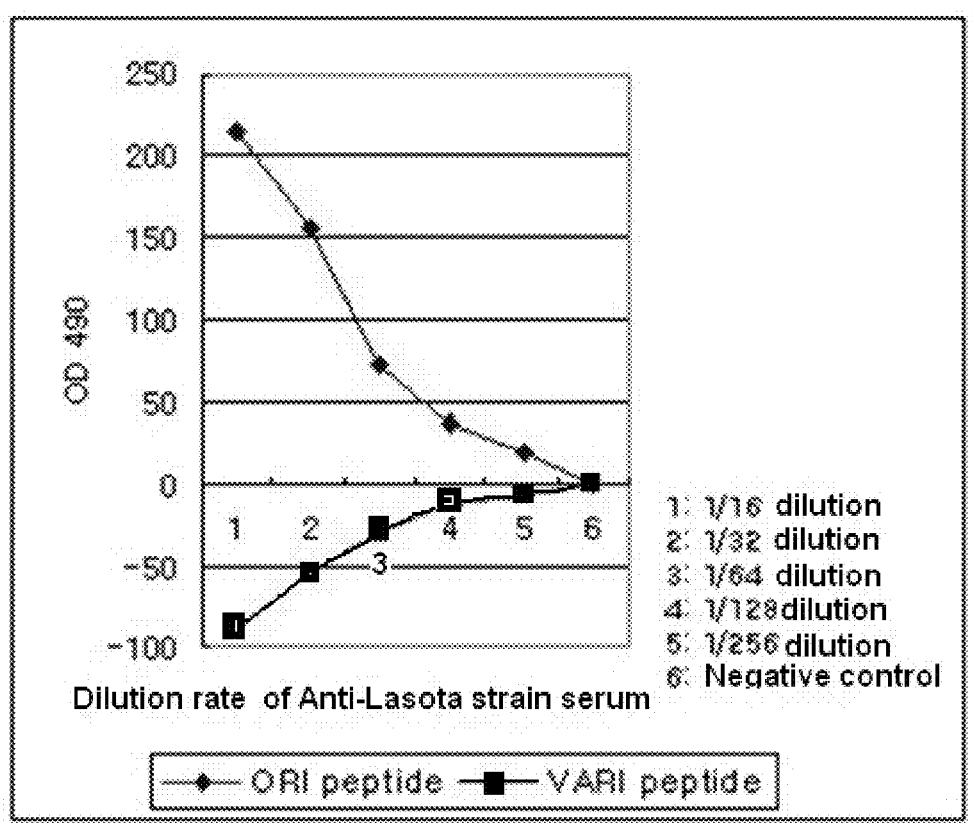
FIG. 2A and FIG. 2B are ELISA results which shows the different reactivity of linear epitope of HN proteins of vaccine strains (La Sota, B1, Ulster) and conventional pathogenic wild-type strains (KWON, Hyuk-Joon, 2000, Doctoral thesis of graduate school of Seoul National University), and a linear epitope of UN proteins in antigenic variant virus of the present invention against anti-La Sota serum and anti-KBNP-4152 serum.
Figure 2B:
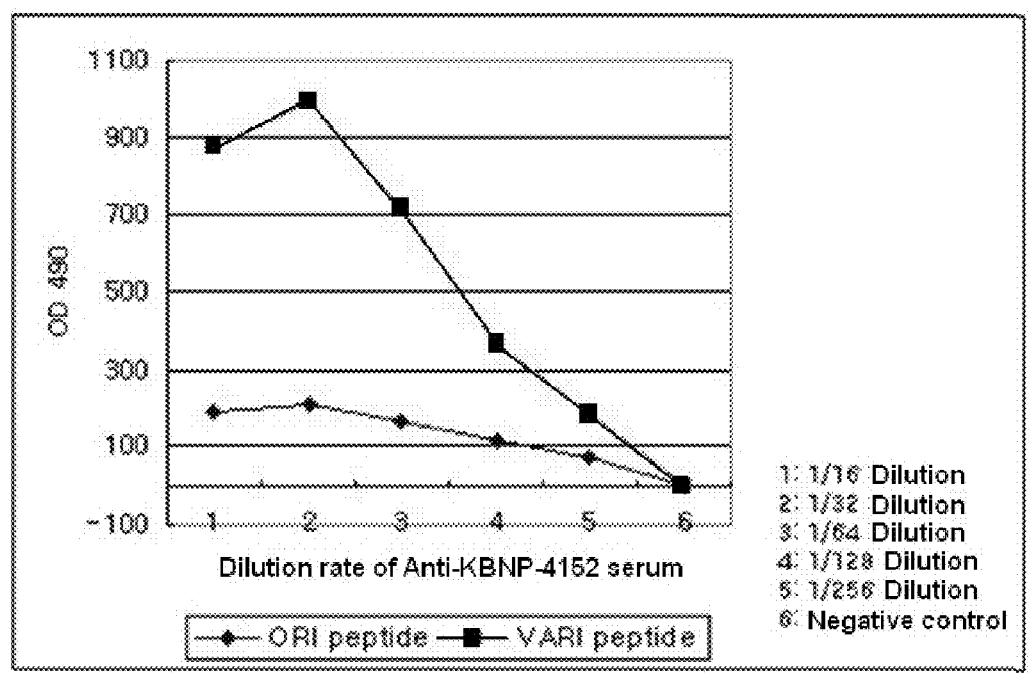

As a result, anti-La Sota strain serum shows high reactivity to a peptide of SEQ ID NO: 2, but low reactivity to a peptide of SEQ ID NO: 6. Anti-KBNP-4152 serum shows high reactivity to a peptide of SEQ ID NO: 6, but low reactivity to a peptide of SEQ ID NO: 2. The result proves for the first time that the linear epitope is recognized by avian immune system. In addition, the result agree recent phenomenon that wild-type Newcastle virus including SEQ ID NO: 6 is scarcely neutralized by conventional vaccine antibody (see FIG. 2).

The present invention relates to an antibody or its fragment which specifically recognizes an epitope of Newcastle disease virus HN protein and comprises an amino acid sequence selected from the group consisting of an amino acid sequence having SEQ ID NO: 2, an amino acid sequence having SEQ ID NO: 4, and an amino acid sequence having SEQ ID NO: 6.

More specifically, the present invention relates to the antibody or its fragment that is produced by using HN protein epitope having an amino acid sequence shown in SEQ ID NO: 2 as an antigen, and specifically recognizes an amino acid sequence shown in SEQ ID NO: 2.

The present invention relates to the antibody or its fragment that is produced by using HN protein epitope having an amino acid sequence shown in SEQ ID NO: 4 as an antigen, and specifically recognizes an amino acid sequence shown in SEQ ID NO: 4.

The present invention relates to the antibody or its fragment that is produced by using HN protein epitope having an amino acid sequence shown in SEQ ID NO: 6 as an antigen, and specifically recognizes an amino acid sequence shown in SEQ ID NO: 6.

The antibody is monoclonal or polyclonal. The fowls are chicken, pheasant, duck, turkey, quail, and ostrich, etc.

In addition, the present invention relates to a method of diagnosing Newcastle disease comprising reacting the antibody or its fragment with a sample including Newcastle disease virus, detecting a positive reaction against the antibody and determining the sample showing the positive reaction as Newcastle disease. The positive reaction can be detected by general detecting method of antigen-antibody reaction, for example ELISA. For example, the positive reaction is detected by marking the antibody or its fragment with a labeling material selected from the group consisting of radioisotope, fluorescent, luminescent, enzyme, chromogen and dye, and detecting the reaction result of the labeling material.

In another embodiment, the present invention relates to a method of diagnosing Newcastle disease comprising reacting the antibody or its fragment with a sample including Newcastle disease virus, detecting haemagglutination inhibition with addition of chicken erythrocyte, and determining the sample showing haemagglutination inhibition as Newcastle disease. The hemagglutination inhibition method can be carried out according to the virus hemagglutination inhibition test which is well known to an ordinary skilled person in the art.

In further embodiment, the present invention relates to a polypeptide kit of diagnosing Newcastle disease comprising the antibody or its fragment which can recognize the HN linear epitope, or a polynucleotide kit of diagnosing Newcastle disease comprising a polynucleotide encoding the HN linear epitope. The polynucleotide kit can be prepared by a) dropping a solution including a buffer solution and a polynucleotide of SEQ ID NO: 1, a polynucleotide of SEQ ID NO: 3, and a polynucleotide of SEQ ID NO: 5 as a probe on a substrate, for example glass coated with Poly-L-lysine, nitrocellulose, or nylon membrane, etc., and b) drying or UV-irradiating. The prepared substrate can be analyzed by southern blotting or northern blotting, after a virus RNA or RT-PCR product is labeled with fluorescent, biotin, digoxigenin, etc. In addition, the prepared substrate can be analyzed by real time PCR. The polynucleotide including a nucleotide sequence encoding HN protein epitope can be useful as a probe in a method for detecting a virus with oligonucleotide microarray.

The present invention provides a vaccine for Newcastle disease comprising a Newcastle disease virus deposited as an accession number KCTC 10919BP comprising an epitope of HN protein having an amino acid sequence as shown in SEQ ID NO: 6.

The Newcastle disease virus including the mutated HN epitope was deposited under Gene Bank of Korea Research Institute of Bioscience and Biotechnology on Mar. 10, 2003 to receive accession number KCTC 10919BP. The virus contains a mutated lysine on $347^{th}$ and $354^{th}$ amino acids of an epitope of HN protein consisting of $345^{th}$ amino acid to $358^{th}$ amino acid. In addition, comparing cysteine residues being important for formation of protein conformation (HN: C1-C13, F: C1-C13), and N-glycosylation region (HN: G1-G6, F: G1-G6) in the mutant virus SNU4152 of the present invention and La Sota strain, C1 and G5 in HN protein, and C2 in F protein are different.

In another embodiment, the present invention relates to a vaccine for Newcastle disease which comprises a Newcastle disease virus deposited as an accession number KCTC 10919BP. The new virus comprises an epitope of HN protein having an amino acid sequence as shown in SEQ ID NO: 6. The vaccine for Newcastle disease is a live vaccine, an attenuated vaccine, or a killed vaccine. The vaccine can further contains conventional acceptable carrier, exipient and additives, for examples, mineral oil, aluminum hydroxide gel, saponin as an adjuvant, vitamins, monosodium glutamate, lipopolysaccharide, BCG, chitosan, glucan, peptidoglucan, etc. The vaccine can be used for the Newcastle disease virus of fowls, such as chicken, pheasant, duck, turkey, quail, and ostrich, etc. The vaccine can be administered to fowls subcutaneously, or intramuscularly, once or repetitively per a day at the time of incubating, before egg-laying, or during egg-laying. The dosage is the same as the general vaccine for Newcastle disease.

F protein of Newcastle disease virus is produced in an inactive precursor form (F0), and cleaved to active forms F1 and F2 at the Golgi membranes [Morrison, T., and A. Portner, *Structure, function, and intracellular processing of the glycoproteins of Paramyxoviridae,* 1991, p. 347-375. In D. Kingsbury (ed.), The Paramyxoviruses. Plenum Press, New York.]. The cleavage exposes N-terminal hydrophobic domain of F1 subunit, which plays an important role in biological activity of mature protein. (Scheid and Choppin, 1974; Scheid and Choppin, 1978). The hydrophobic domain named as fusion peptide is well conserved in F protein of Paramyxovirus, and involves in membrane fusion directly (Lamb, 1993). F protein of Paramyxovirus includes the common structural characteristics such as the heptad repeats, and two regions being capable of forming alpha-helix (Lamb, 1993). Heptad repeat A is adjacent to N-terminal hydrophobic fusion protein of F1, Heptad repeat B is close to the upper part of transmembrane region. Heptad repeat B includes well-conserved Leucine or Isoleucine at every 7 residues (Buckland and Wild, 1989).

HN protein makes virion locate on the host cell surface via binding to sialic acids of glycoconjugates. HN protein is divided into three regions, transmembrane domain, stalk domain and globular domain. Both a binding site of antigenic receptor and an active site of neuraminidase are the globular domain. Fusion induction activity is the stalk domain, and interacts with F protein (Sergei et al., 1993). The expected structure of the stalk domain have alpha-helix, two heptad repeats including heptad repeat A ($74-88^{th}$ amino acids) and heptad repeat B ($96-110^{th}$ amino acids). It has reported that any mutation breaking the structure reduces the receptor binding and neuraminidase activity (Stone-Hulslander and Morrison, 1999).

Figure 3:
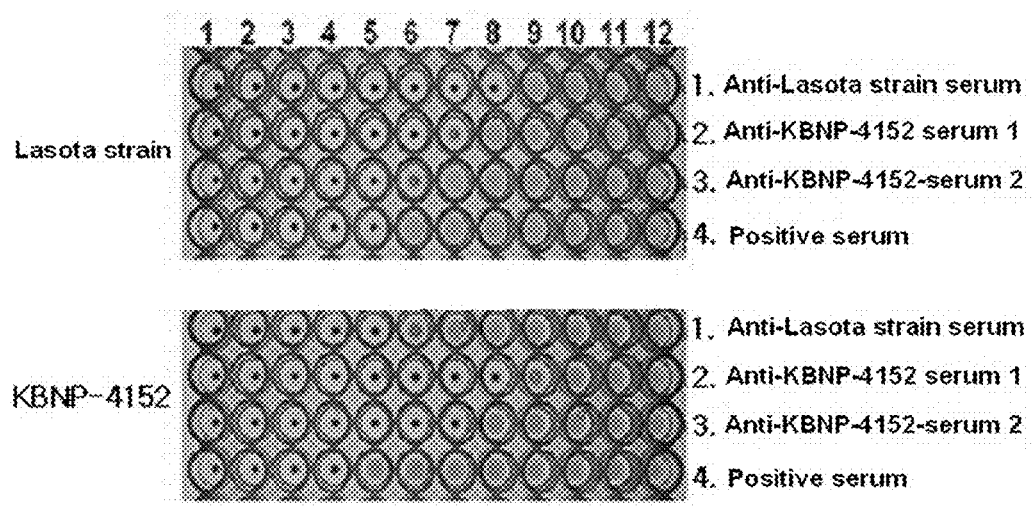
FIG. 3 are a result of hemagglutination inhibition test that the anti-La Sota serum and anti-KBNP-4152 serum are reacted with a linear epitope of HN protein of La Sota vaccine strain and a novel linear epitope of HN protein in antigenic variant strain (KBNP-4152).

In another embodiment, the cross hemagglutination-inhibition test is performed on KBNP-0028 including an amino acid of SEQ ID NO: 6 and La Sota strain. Consequently, anti-La Sota strain serum shows higher hemagglutination-inhibition titer against La Sota strain, but 4 to 8 times as low as hemagglutination-inhibition titer of anti-KBNP-4152. Hemagglutination-inhibition titer of anti-KBNP-4152 serum against KBNP-4152 is 4 to 8 times as high as anti-La Sota serum. La Sota strain including an amino acid sequence of SEQ ID NO: 1 has antigenic difference from KBNP-4152 including an amino acid sequence of SEQ ID NO: 6(see FIG. 3).

In addition, the virus neutralization test is carried out by respectively neutralizing KBNP-4152 with anti-La Sota strain serum and anti-KBNP-4152 serum, and infecting chick embryo fibroblast. As a result, the virus neutralizing activity of anti-La Sota strain serum is 128 times as low as that of anti-KBNP-4152 serum. The result means that La Sota strain and KBNP-4152 are different in antigenicity (see FIG. 4).

The present invention is further explained in more detail with reference to the following examples. These examples, however, should not be interpreted as limiting the scope of the present invention in any manner.

EXAMPLE 1

Nucleotide Sequence ANALYSIS of a Linear Epitope of HN Protein

<1-1> Isolation of a Virus Strain

Newcastle virus strains were isolated from a chicken by a standard method (Alexander, 1989). More specifically, the viruses were isolated from hemorrhagic lesion samples of trachea, proventriculus, small intestine, and cecal tonsils. The isolated viruses were inoculated on chicken embryo fibroblasts cultured in a DMEM (Gibco/BRL, Grand Island, N.Y.) media containing 10% BCS (bovine calf serum, Gibco/BRL, Grand Island, N.Y.), and then, cultured under the humidified conditions of 5% $CO_2$ and 37° C.

After observing the syncytia, the supernatant was inoculated into allantoic cavity of 10- to 11-day old SPF (specific pathogen free) embryonated chicken eggs (Sunrise Co., NY), cultured at 37° C. for 3 days, and left at 4° C. Thereafter, the allantoic fluids were collected. The collected allantoic fluids were subjected to chicken erythrocyte agglutination and bacterial infection tests. SNUO202, KBNP-4152, SNU5005, SNU5009, SNU5070, and SNU5074 were used to analyze the nucleotide sequences of HN protein linear epitopes. The final identification of Newcastle disease virus was performed based on the nucleotide sequences determined in Example 1-3. Partial nucleotide sequences of HN protein used for virus identification and linear antigen analysis were shown in SEQ ID Nos: 10 to 15, and FIG. 5A to 5F.

TABLE 1

Strain Sources

| Strain | Species | Farm Location | Age (days) | Clinical Symptoms** |
|---|---|---|---|---|
| KBNP-4152 | Egg-Layer | Naju | 41 | Respiratory failure and death (25%) |
| SNU0202 | Egg-Layer | Anseong | 28 | Death |
| SNU5070 | White stork | Cheongju | — | Death |
| SNU5005 | Egg type breeder | Pyeongtaek | 193 | Decrease of egg production |
| SNU5009 | Egg-Layer | Pyeongtaek | 31 | Respiratory failure and death |
| SNU5074 | Rufous turtle dove | Cheorwon | — | Death |

<1-2> Isolation of RNA and RT-PCR

Viral genomic RNA was extracted from the allantoic fluid by an acid-guanidinium-phenol method (Chomzinski and Sacci, 1985). More specifically, 100 μl of the allantoic fluid was added to 1 ml of TRI reactant (MRC co., MA), to extract RNA. The RNA precipitate was dissolved in 50 μl of distilled water (DW) treated with 0.1% DEPC (diethyl pyrocarbonate).

1 μl of the extracted RNA, 1 μl of random hexamer (20 ng/μl), 2 μl of 5×1$^{st}$ stranded buffer, and 4.5 μl of DEPC-treated DW were sufficiently mixed, and reacted at 72° C. for 15 minutes, and cooled. 1 μl of dNTPs (Bioneer co., Korea) and 0.5 μl of MMLV reverse transcriptase (Superscript II, Gibco, BRL) were added to the reacted mixture, and reacted at 42° C. for 60 minutes. The reverse transcriptase was inactivated by treating at 94° C. for 5 minutes.

1 μl of four-times diluted cDNA, 1 μl of 10×PCR buffer, 0.2 μl of 2.5 mM dNTPs, 2 μl of each primer (SEQ ID NOs: 7 and 8), 1 μl of Taq polymerase (Bioneer co., 1 U/μl) and 7.2 μl of DW were mixed. The mixture was denaturated at 94° C. for 4 minutes. Then, the mixture was treated at 94° C. for 30 seconds, at 52° C. for 10 seconds, and at 72° C. for 60 seconds, which is repeated 35-times, and then further reacted at 72° C. for 7 minutes. The PCR product was analyzed through electrophoresis in 2% agarose gel and staining with EtBr.

As a result, an amplified product having an expected size was observed, and the analysis of the nucleotide sequence thereof revealed that it corresponded to a specific band.

<1-3> Analysis of Nucleotide Sequence

The nucleotide sequence analysis of HN protein coding gene was performed using ABI377 DNA autoanalyzer and dye terminator kit (Perkin Elmer, Foster, Calif.) (Kwon et al., 2000). More specifically, 5 μl of PCR product was added to 1 μl of 3 M sodium acetate (pH 5.2) and 12.5 μl of 95% ethanol, and left in ice for 10 minutes. Then, the mixture was centrifuged at 14,000 rpm for 15 minutes, and washed with 70% ethanol. The obtained precipitate was dried and dissolved in 10 μl of 1×PCR buffer.

In order to economically analyze the nucleotide sequence, the dye terminator kit (Taq polymerase, FS; Perkin Elmer Co.) was diluted 2.5 times with DW. 2 μl of the diluted kit was added to 1 μl of DNA, 2 μl of 1×PCR buffer, and 1 μl of primer for determining nucleotide sequence (SEQ ID NO: 9, 3 pmol/μl). After reaction at 96° C. for 10 seconds, PCR was performed at 96° C. for 10 seconds, at 56° C. for 5 seconds and at 60° C. for 20 seconds, which is repeated 25 times, and then completed at 4° C. After the PCR was completed, the PCR product was precipitated in ethanol. The precipitate was dried and dissolved in 2 μl of Blue Dextran/EDTA (Perkin Elmer Co.) loading buffer (5 volumes of formamide and 1 volume of blue dextran/EDTA). After denaturation, a reaction was conducted using ABI377 DNA autoanalyzer.

Figure 1:
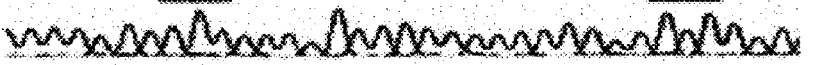
FIG. 1 shows the amino acid sequence alignment of linear epitopes ($345^{th}$-$355^{th}$ amino acid) of HN proteins in Newcastle disease virus.

As the result, it is found that SNUO202 contains the nucleotide sequence of SEQ ID NO: 2, SNU5070 contains the nucleotide sequence of SEQ ID NO: 4, and KBNP-4152, SNU5005, SNU5009 and SNU5074 contain the nucleotide sequence of SEQ ID NO: 6 (see FIG. 1).

<1-4> Comparative Analysis with Other Strains

The amino acid sequences of the linear epitopes of the analyzed HN proteins were analyzed through protein-protein BLAST search (www.ncbi.nlm.nih.gov/blast).

As a result, the HN linear epitope of SEQ ID NO: 1 is observed in most of Newcastle disease viruses including vaccine strains La Sota, B1, and Ulster. The HN linear epitope of SEQ ID NO: 2 is observed in strains SL03(ABB45815), JS06(ABB45825), SGM01(ABB45828), TJ03(ABB51144), SBZ02(ABB51145), JS01 (ABB51146), JS02(ABB51147), JS04(ABB51148), JS05(ABB51149), SCL03(ABB51151), SQD04(ABB51152), JS03(ABB51154), GD05 (ABC86693), wfan-3-01 (AAY46244), ytan-1-01 (AAAY56378), P35742(IBA/85), SNU9358GG (Kwon et al., 2000), SNU9444 (Kwon et al., 2000), and SNU9598 (Kwon et al., 2000). The HN linear epitope of SEQ ID NO: 3 is not observed in foreign Newcastle disease viruses.

EXAMPLE 2

Examination on Chicken Antibody Reactivity of the HN Linear Epitope

<2-1> Peptide Synthesis

The peptides of SEQ ID NO: 1 and SEQ ID NO: 3 were synthesized using Fmoc-Chemistry (Gloor et al., 1994) (Peptron, Daejeon, Korea). In order to increase the coating efficiency on 96-well plate, 7 lysine residues were attached to amino-terminus of SEQ ID NO: 1, and 4 aminocaproic acid residues were attached to carboxyl-terminus of SEQ ID NO: 3.

<2-2> Preparation of Antiserum

La Sota strain (hemagglutination titer 1,024/25 µl) was inactivated by 0.2% formalin, and KBNP-4152(hemagglutination titer 248/25 µl) was inactivated by 0.025% formalin. Each of these viruses was inoculated into 5 SPF embryonic chicken eggs in the amount of 200 µl per each egg, and observed for 3 days. The allantoic fluids were collected, and subjected to hemagglutination test, indicating that they are negative. Complete Freund's adjuvant and the inactivated virus were mixed in the same amount, to make a water-in-oil emulsion. The emulsion was inoculated into 2 SPF chickens in the amount of 200 µl per each chicken. 2 chickens were raised for the experimental period as negative-control groups, and examined whether it is negative to the Newcastle virus. Blood samples were taken at 4 weeks after vaccine inoculation, and sera were separated therefrom and kept refrigerated or frozen state for following experiments.

<2-3> ELISA

Peptides of SEQ ID NO: 2 and SEQ ID NO: 6 were suspended in 50 mM carbonate-bicarbonate (pH9.6) buffer solution, and coated on 96-well plate at the room temperature for 4 hours, wherein the amounts of the peptides coated in each well were 125 ng and 4 µg, respectively. Then, 200 µl of 3% bovine serum albumin was added thereto, blocking overnight at 4° C. The blocking solution was washed with phosphate buffer (pH7.2). Then, anti-La Sota serum and anti-KBNP-4152 serum were diluted 16-times, 32-times, 128-times and 256-times, respectively. The diluted anti-serum was added to the well on which each peptide is coated, allowed to react at the room temperature for 1 hour, and then washed three times with phosphate buffer. Anti-chicken immunoglobulin-HRP conjugated secondary antibody was added thereto, allowed to react at the room temperature for 1 hour, and then washed three times with phosphate buffer. Thereafter, a matrix solution (TMB, 3,3',5,5'-Tetramethylbenzidine) was added, and then a quenching solution was added to measure the absorbance at 450 nm. The measured absorbance was compensated by deduction of the absorbance of the well which does not containing serum and that of the well which is not coated with the peptide.

As a result, anti-La Sota strain serum exhibits a high reactivity to the peptide of SEQ ID NO: 2, whereas no reactivity to the peptide of SEQ ID NO: 6. Anti-KBNP-4152 serum exhibits a high reactivity to the peptide of SEQ ID NO: 6 (see FIG. 4), Therefore, it is found for the first time that the peptides of SEQ ID NO: 2 and SEQ ID NO: 6 can be recognized by the avian immune system. Further, it is shown that the change in the amino acid sequence of SEQ ID NO: 6 results in altering the antigenicity, thereby causing a sudden decrease of antibody's activity to the existing vaccine strains.

EXAMPLE 3

Cross Hemagglutination Inhibition Test

For a unidirectional hemagglutination inhibition test, the hemagglutination titers of La Sota and KBNP-4152 strains were measured. More specifically, 50 µl of phosphate buffer was sprayed on each well of 96-well plate. 50 µl of virus was added to the first well and mixed. Then, 50 µl of the mixture was collected from the first well, and added to the next well and mixed. The above adding and mixing process was repeated, and 50 µl of the mixture collected from the last well was removed, to perform serial dilutions. 50 µl of 0.5% (v/v) chicken erythrocyte was added to each well, wherein the concentrations of virus in the wells were serially diluted by two-fold unit as above, and allowed to react at 4° C. for 30 minutes. The dilution factor ($2^n$, n=Dilution Factor) of the well where the hemagglutination is completely accomplished was used as the hemagglutination titer.

On the basis of the obtained titer, the cross hemagglutination inhibition test was performed. That is, 25 µl of La Sota strain with 4-hemagglutination units and 25 µl of anti-La Sota strain serum, 25 µl of La Sota strain and 25 µl of anti-KBNP-4152 serum, 25 µl of KBNP-4152 and 25 µl of anti-KBNP-4152 serum, 25 µl of KBNP-4152 and 25 µl of anti-La Sota strain serum were mixed at the room temperature for 30 minutes. Then, 50 µl of 0.5% chicken erythrocytes were added thereto. After 30 minutes at 4° C., the number of the wells where the hemagglutination is completely inhibited was used as the hemagglutination inhibition titer.

As a result, the anti-La Sota strain serum shown a high hemagglutination inhibition titer to the La Sota strain, whereas anti-KBNP-4152 serum exhibits a low hemagglutination inhibition titer thereto which is 4- to 8-times lower than that of the anti-La Sota strain serum. Anti-KBNP-4152 serum exhibits a high hemagglutination inhibition titer to the KBNP-4152 virus which is 4- to 8-times higher than that of the anti-La Sota strain serum. These results reveal again that there is difference in the antigenicity between the La Sota strain of SEQ ID NO: 2 and KBNP-4152 of SEQ ID NO: 6 (see FIG. 3).

EXAMPLE 4

Unidirectional Virus Neutralization Test

In order to examine the neutralization ability of the antibodies produced by the inoculation of La Sota strain and KBNP-4152, a unidirectional virus neutralization test was performed. More specifically, serum was diluted two times by PBS in a test tube, and transferred to 96-well plate in the amount of 100 µl per a well. Then, the same amount of virus (100 $TCID_{50}$/25 µl) was added, and neutralized at 37° C. for 1 hour. 25 µl of the neutralized material and 100 µl of fibroblast suspension were inoculated into each well, and cultured at 37° C. for 4 days. The reciprocal of the maximum dilution factor, where the neutralization is completely accomplished, and no cytopathogenic effect occurs, was used as the neutralization titer.

Figure 4:
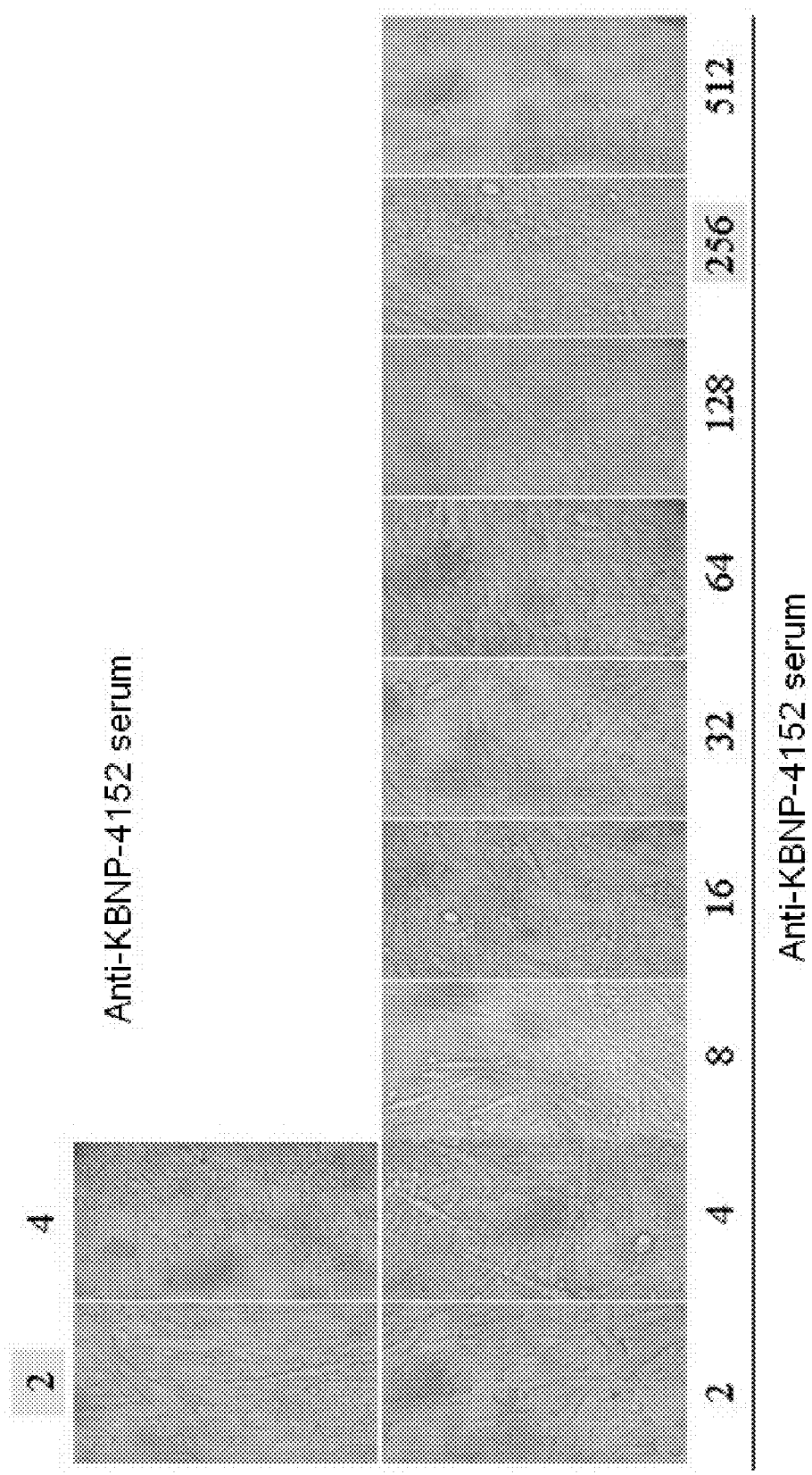
FIG. 4 shows a result of virus neutralization test that anti-La Sota serum and anti-KBNP-4152 serum are reacted with KBNP-4152, FIG. 5a to FIG. 5f represents a nucleotide sequence of HN protein according to the present invention(SEQ ID NOs: 10-15, respectively).

As a result, it is found that the neutralization ability of the anti-La Sota strain serum is 128 times lower than that of anti-KBNP-4152 serum, to confirm the difference in the antigenicity between the two viruses (see FIG. 4).

As above described, in the present invention, the HN epitope of that is recognized by the immune system of fowls and the Newcastle disease virus in which the epitope is modified can be used in developing efficient vaccines, and further, in diagnosing the Newcastle disease virus rapidly and exactly.

The invention claimed is:

1. An isolated polypeptide comprising an epitope of HN protein of Newcastle disease virus, said polypeptide comprising SEQ ID NO: 6.

2. An isolated peptide which is an epitope of HN protein of Newcastle disease virus, said peptide consisting of SEQ ID NO: 6.

3. An isolated Newcastle disease virus deposited as accession number KCTC 10919BP.

4. A killed vaccine for Newcastle disease which comprises the Newcastle disease virus deposited as accession number KCTC 10919BP.

* * * * *

SEQUENCE LISTING

<160> NUMBER OF SEQ ID NOS: 15

<210> SEQ ID NO 1
<211> LENGTH: 42
<212> TYPE: DNA
<213> ORGANISM: Newcastle disease virus
<220> FEATURE:
<221> NAME/KEY: CDS
<222> LOCATION: (1)..(42)

<400> SEQUENCE: 1 ccc gat gaa caa gat tac caa att cgg atg gct aag tct tca        42
Pro Asp Glu Gln Asp Tyr Gln Ile Arg Met Ala Lys Ser Ser
  1               5                  10

<210> SEQ ID NO 2
<211> LENGTH: 14
<212> TYPE: PRT
<213> ORGANISM: Newcastle disease virus

<400> SEQUENCE: 2

Pro Asp Glu Gln Asp Tyr Gln Ile Arg Met Ala Lys Ser Ser
  1               5                  10

<210> SEQ ID NO 3
<211> LENGTH: 42
<212> TYPE: DNA
<213> ORGANISM: Newcastle disease virus
<220> FEATURE:
<221> NAME/KEY: CDS
<222> LOCATION: (1)..(42)

<400> SEQUENCE: 3 ccc gat aaa caa gat tac caa att cgg atg gct aag tct tca        42
Pro Asp Lys Gln Asp Tyr Gln Ile Arg Met Ala Lys Ser Ser
  1               5                  10

<210> SEQ ID NO 4
<211> LENGTH: 14
<212> TYPE: PRT
<213> ORGANISM: Newcastle disease virus

<400> SEQUENCE: 4

Pro Asp Lys Gln Asp Tyr Gln Ile Arg Met Ala Lys Ser Ser
  1               5                  10

<210> SEQ ID NO 5
<211> LENGTH: 42
<212> TYPE: DNA
<213> ORGANISM: Newcastle disease virus
<220> FEATURE:
<221> NAME/KEY: CDS
<222> LOCATION: (1)..(42)

<400> SEQUENCE: 5 ccc gat aaa caa gat tac caa att cgg aag gct aag tct tca        42
Pro Asp Lys Gln Asp Tyr Gln Ile Arg Lys Ala Lys Ser Ser
  1               5                  10

<210> SEQ ID NO 6
<211> LENGTH: 14
<212> TYPE: PRT
<213> ORGANISM: Newcastle disease virus

<400> SEQUENCE: 6

Pro Asp Lys Gln Asp Tyr Gln Ile Arg Lys Ala Lys Ser Ser
 1               5                   10

<210> SEQ ID NO 7
<211> LENGTH: 30
<212> TYPE: DNA
<213> ORGANISM: Artificial Sequence
<220> FEATURE:
<223> OTHER INFORMATION: PRIMER

<400> SEQUENCE: 7
ccgcggcacc gacaacaaga gtcaatcatg                                    30

<210> SEQ ID NO 8
<211> LENGTH: 31
<212> TYPE: DNA
<213> ORGANISM: Artificial Sequence
<220> FEATURE:
<223> OTHER INFORMATION: PRIMER

<400> SEQUENCE: 8
ctcaactagt aagggaacga tcctaaattc c                                  31

<210> SEQ ID NO 9
<211> LENGTH: 20
<212> TYPE: DNA
<213> ORGANISM: Artificial Sequence
<220> FEATURE:
<223> OTHER INFORMATION: PRIMER

<400> SEQUENCE: 9
atactatccg gttgcagaga                                               20

<210> SEQ ID NO 10
<211> LENGTH: 536
<212> TYPE: DNA
<213> ORGANISM: Newcastle disease virus SNU0202

<400> SEQUENCE: 10
gcttcggaca tctgcaacag ggagggtatt cttttctact ctgcgctcca tcaatttaga    60
tgacacccaa aatcggaagt cctgcagtgt gagtgcaacc cctttaggtt gtgatatgct   120
gtgctctaag gtcacaggga ctgaagagga ggattacaag tcagttgccc ccacatcaat   180
ggtgcacgga aggctagggt tgacggtca ataccatgaa aaggacttag acaccacggt   240
cttatttaag gattgggtgg caaattaccc aggagcggga ggagggtctt ttattgacga   300
ccgtgtatgg ttcccagttt acggagggct caaacccaat tcacccagtg acactgcaca   360
agaagggaaa tacgtaatat acaagcgcca taacaacaca tgccccgatg aacaagatta   420
ccaaattcgg atggctaagt cttcatataa acccgggcga tttggtggaa agcgcgtaca   480
gcaagccatc ttatccatca agtgtcaac atccttgggt aaggacccgg tgctga       536

<210> SEQ ID NO 11
<211> LENGTH: 536
<212> TYPE: DNA
<213> ORGANISM: Newcastle disease virus SNU5005

<400> SEQUENCE: 11
gcttcggaca tctgcaacag ggagggtatt cttttctact ctgcgctcca tcaatttaga    60
tgacacccaa aatcggaagt cctgcagtgt gagtgcaacc cctttaggtt gtgatatgct   120

```
gtgctccaag gtcacaggga ctgaagagga ggattacaag tcagttgccc ccacatcaat    180
ggtgcacgga aggctagggt tgacggtca ataccatgaa aaggacttag acaccacggt    240
cttatttaag gattgggtgg caaattaccc aggagcggga ggagggtctt ttattgacga    300
ccgtgtatgg ttcccagttt acggagggct caaacccgat tcacccagtg acactgcaca    360
agaagggaaa tacgtaatat acaagcgcca taacaacaca tgccccgata aacaagatta    420
ccaaattcgg aaggctaagt cttcatataa acccggggcga tttggtggga agcgcataca   480
gcaagccatc ttatccatca aagtgtcaac atccttgggt aaggacccgg tgctga        536

<210> SEQ ID NO 12
<211> LENGTH: 536
<212> TYPE: DNA
<213> ORGANISM: Newcastle disease virus SNU5009

<400> SEQUENCE: 12
gcttcggaca tctgcaacag ggagggtatt cttttctact ctgcgctcca tcaatttaga     60
tgacacccaa aatcggaagt cctgcagtgt gagtgcaacc cctttaggtt gtgatatgct    120
gtgctccaag gtcacaggga ctgaagagga ggattacaag tcagttgccc ccacatcaat    180
ggtgcacgga aggctagggt tgacggtca ataccatgaa aaggacttag acaccacggt    240
cttatttaag gattgggtgg caaattaccc aggagcggga ggagggtctt ttattgacga    300
ccgtgtatgg ttcccagttt acggagggct caaacccgat tcacccagtg acactgcaca    360
agaagggaaa tacgtaatat acaagcgcca taacaacaca tgccccgata aacaagatta    420
ccaaattcgg aaggctaagt cttcatataa acccggggcga tttggtggga agcgcataca   480
gcaagccatc ttatccatca aagtgtcaac atccttgggt aaggacccgg tgctga        536

<210> SEQ ID NO 13
<211> LENGTH: 536
<212> TYPE: DNA
<213> ORGANISM: Newcastle disease virus SNU5070

<400> SEQUENCE: 13
gcttcggaca tctgcaacag ggagggtatt cttttctact ctgcgctcca tcaatttaga     60
tgacacccaa aatcggaagt cctgcagtgt gagtgcaacc cctttaggtt gtgatatgct    120
gtgctctaag gtcacaggga ctgaagagga ggattacaag tcagttgccc ccacatcaat    180
ggtgcgcgga aggctagggt tgacggtca ataccatgaa aaggacttag acaccacggt    240
cttatttaag gattgggtgg caaattaccc aggagcggga ggagggtctt ttattgacga    300
ccgtgtatgg ttcccagttt acggagggct caaacccaat tcacccagtg acaccacaca    360
agaagggaaa tacgtaatat acaagcgcca taacaacaca tgccccgata aacaagatta    420
ccaaattcgg atggctaagt cttcatataa acccaggcga tttggtggaa agcgcgtaca   480
gcaagccatc ttatccatca aagtgtcaac atccttgggt aaggacccgg tgctga        536

<210> SEQ ID NO 14
<211> LENGTH: 536
<212> TYPE: DNA
<213> ORGANISM: Newcastle disease virus SNU5074

<400> SEQUENCE: 14
gcttcggaca tctgcaacag ggagggtatt cttttctact ctgcgctcca tcaatttaga     60
tgacacccaa aatcggaagt cctgcagtgt gagtgcaacc cctttaggtt gtgatatgct    120
gtgttccaag gtcacaggga ctgaagagga ggattacaag tcagttgccc ccacatcaat    180
```

-continued

```
ggtgcacgga aggctagggt ttgacggtca ataccatgaa aaggacttag acaccacggt    240
cttatttaag gattgggtgg caaattaccc aggagcggga ggagggtctt ttattgacga    300
ccgtgtatgg ttcccagttt acggagggct caaacccgat tcacccagtg acactgcaca    360
agaagggaaa tacgtaatat acaagcgcca taacaacaca tgtcccgata aacaagatta    420
ccaaattcgg aaggctaagt cttcatataa acccgggcga tttggtggga agcgcgtaca    480
gcaagccatc ttatccatca aagtgtcaac atccttaggt aaggacccgg tgctga        536

<210> SEQ ID NO 15
<211> LENGTH: 536
<212> TYPE: DNA
<213> ORGANISM: Newcastle disease virus KBNP-4152

<400> SEQUENCE: 15
gcttcggaca tctgcaacag ggagggtatt cttttctact ctgcgctcta tcaatttaga     60
tgacacccaa aatcggaagt cctgcagtgt gagtgcaacc cctttaggtt gtgatatgct    120
gtgctccaag gtcacaggga ctgaagagga ggattacaag tcagttgccc ccacatcaat    180
ggtgcacgga aggctagggt ttgacggtca ataccatgaa aaggacttag acaccacggt    240
cttatttaag gattgggtgg caaattaccc aggagcggga ggagggtctt ttattgacga    300
ccgtgtatgg ttcccagttt acggagggct caaacccgat tcacccagtg acactgcaca    360
agaagggaaa tacgtaatat acaagcgcca taacaacaca tgccccgata aacaagatta    420
ccaaattcgg aaggctaagt cttcatataa acccgggcga tttggtggga agcgcgtaca    480
gcaagccatc ttatccatca aagtgtcaac atctttgggt aaggacccgg tgctga        536
```